(12) United States Patent
Song et al.

(10) Patent No.: US 10,414,711 B2
(45) Date of Patent: Sep. 17, 2019

(54) METHOD OF PREPARING (METH)ACRYLIC ACID

(71) Applicant: LG CHEM, LTD., Seoul (KR)

(72) Inventors: Jong Hun Song, Daejeon (KR); Se Won Baek, Daejeon (KR); Sul Hee Yoo, Daejeon (KR); Yoon Jae Min, Daejeon (KR)

(73) Assignee: LG CHEM, LTD., Seoul (KR)

( * ) Notice: Subject to any disclaimer, the term of this patent is extended or adjusted under 35 U.S.C. 154(b) by 0 days.

(21) Appl. No.: 15/752,815

(22) PCT Filed: Nov. 21, 2016

(86) PCT No.: PCT/KR2016/013416
§ 371 (c)(1),
(2) Date: Feb. 14, 2018

(87) PCT Pub. No.: WO2017/090948
PCT Pub. Date: Jun. 1, 2017

(65) Prior Publication Data
US 2018/0305288 A1 Oct. 25, 2018

(30) Foreign Application Priority Data

Nov. 27, 2015 (KR) .................. 10-2015-0167714
Oct. 7, 2016 (KR) .................. 10-2016-0129467

(51) Int. Cl.
| | |
|---|---|
| C07C 51/347 | (2006.01) |
| C07C 51/48 | (2006.01) |
| C07C 51/44 | (2006.01) |
| C07C 51/09 | (2006.01) |
| C07C 57/04 | (2006.01) |
| C07C 67/58 | (2006.01) |
| C07C 67/54 | (2006.01) |
| C07C 69/54 | (2006.01) |

(52) U.S. Cl.
CPC ............ *C07C 51/347* (2013.01); *C07C 51/09* (2013.01); *C07C 51/44* (2013.01); *C07C 51/48* (2013.01); *C07C 57/04* (2013.01); *C07C 67/54* (2013.01); *C07C 67/58* (2013.01); *C07C 69/54* (2013.01)

(58) Field of Classification Search
CPC ....... C07C 51/09; C07C 51/347; C07C 67/58; C07C 51/44
See application file for complete search history.

(56) References Cited

U.S. PATENT DOCUMENTS

| | | | |
|---|---|---|---|
| 6,348,135 B1 | 2/2002 | Nakahara et al. | |
| 6,995,282 B1 | 2/2006 | Fauconet et al. | |
| 7,135,594 B2 | 11/2006 | Yada et al. | |
| 7,294,240 B2 | 11/2007 | Geisendoerfer et al. | |
| 7,342,130 B2 | 3/2008 | Shibusawa et al. | |
| 7,348,455 B2 * | 3/2008 | Yada ................. | B01D 3/14 562/545 |
| 8,044,237 B2 | 10/2011 | Briegel et al. | |
| 2004/0220426 A1 | 11/2004 | Yada et al. | |
| 2004/0225149 A1 | 11/2004 | Yada et al. | |
| 2006/0205979 A1 | 9/2006 | Yada et al. | |
| 2009/0253934 A1 | 10/2009 | Ho et al. | |

FOREIGN PATENT DOCUMENTS

| | | |
|---|---|---|
| CN | 103193618 A | 7/2013 |
| EP | 1818324 A1 | 8/2007 |
| JP | 1045670 A | 2/1998 |
| JP | 2001122909 A | 5/2001 |
| JP | 2003171342 A | 6/2003 |
| JP | 2003252825 A | 9/2003 |
| JP | 2005506958 A | 3/2005 |
| JP | 2005170931 A | 6/2005 |
| JP | 2005179352 A | 7/2005 |
| JP | 2005272308 A | 10/2005 |
| JP | 2008214320 A * | 9/2008 |
| JP | 2008214320 A | 9/2008 |
| JP | 4192465 B2 | 12/2008 |
| JP | 4242964 B2 | 3/2009 |
| JP | 2013173801 A | 9/2013 |
| JP | 5715318 B2 | 5/2015 |
| KR | 20040033335 A | 4/2004 |
| KR | 100530967 B1 | 11/2005 |
| KR | 20070059972 A | 6/2007 |
| KR | 20110113036 A | 10/2011 |
| KR | 101091736 B1 | 12/2011 |
| KR | 20140027566 A | 3/2014 |

* cited by examiner

Primary Examiner — Paul A Zucker
(74) Attorney, Agent, or Firm — Dentons US LLP

(57) ABSTRACT

A method of preparing (meth)acrylic acid by using a reaction distillation apparatus including a reaction distillation tower, and a natural circulation type of heat exchanger as a heat source for the reaction distillation tower. The reaction distillation tower a vessel, where decomposition of Michael adducts occurs, connected to a distillation tower, where distillation of decomposition products occurs. The method includes the following steps: feeding a waste liquid to the reaction distillation apparatus after passing through the heat exchanger, wherein the waste liquid is fed to a lower portion of the heat exchanger via a first input port; feeding a gas, separately from the waste liquid via a second input port, to the lower portion of the heat exchanger, and producing and recovering (meth)acrylic acid while the waste liquid is circulated in the reaction distillation apparatus by the gas which is fed separately from the waste liquid.

10 Claims, 2 Drawing Sheets

[FIG. 1]
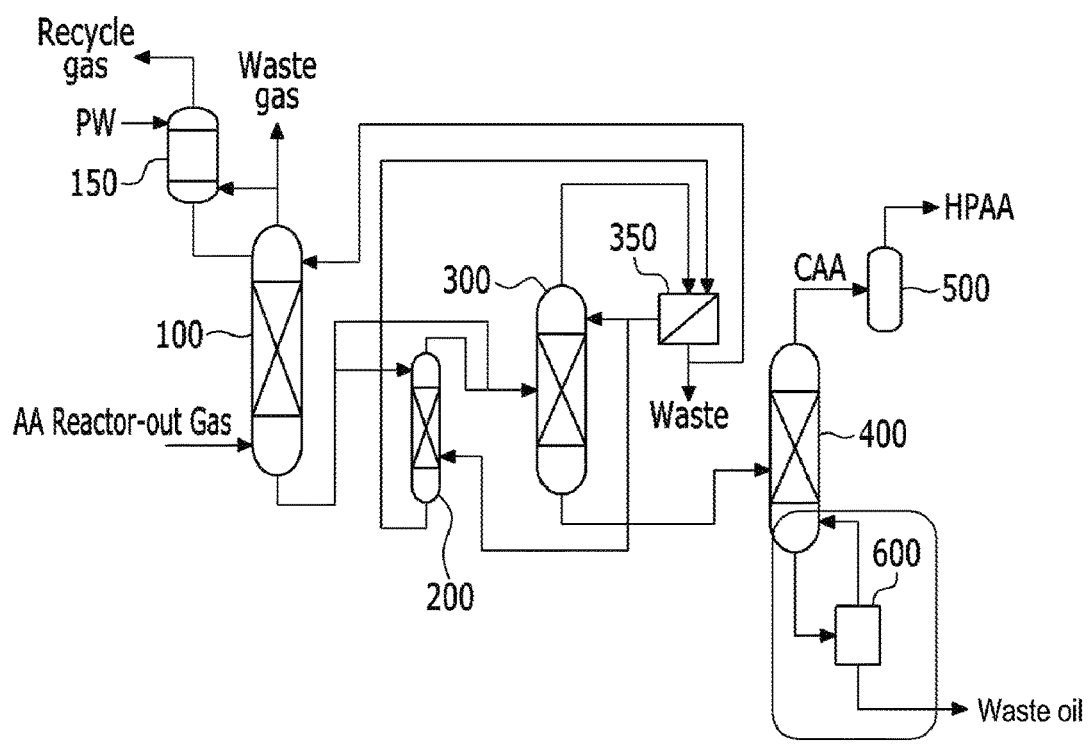

[FIG. 2]
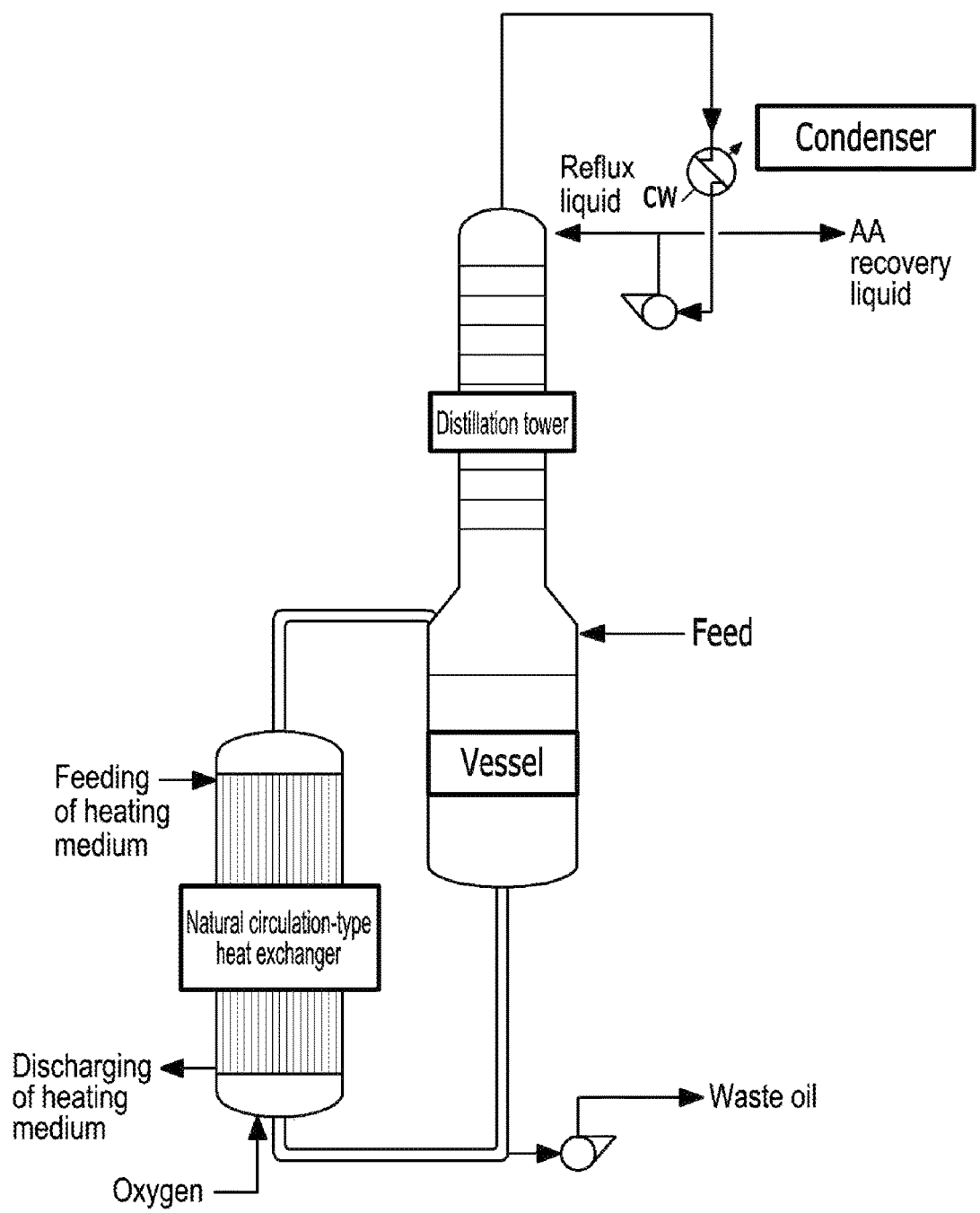

METHOD OF PREPARING (METH)ACRYLIC ACID

CROSS-REFERENCE TO RELATED APPLICATION

This application is a National Stage of International Application No. PCT/KR2016/013416, filed on Nov. 21, 2016, and claims the benefit of and priority to Korean Application No. 10-2015-0167714, filed on Nov. 27, 2015, and Korean Application No. 10-2016-0129467, filed on Oct. 7, 2016 all of which are hereby incorporated by reference in their entirety for all purposes as if fully set forth herein.

TECHNICAL FIELD

The present disclosure relates to a method of preparing (meth)acrylic acid.

BACKGROUND OF ART (Meth)acrylic acid is generally prepared by gas-phase oxidation of a compound such as propane, propylene, (meth)acrolein, etc. in the presence of a catalyst. For example, propane, propylene, etc. is converted into (meth)acrylic acid through (meth)acrolein by gas-phase oxidation in the presence of an appropriate catalyst in a reactor, and a mixed gas of reaction products containing (meth)acrylic acid, non-reacted propane or propylene, (meth)acrolein, an inert gas, carbon dioxide, water vapor, and various organic by-products (acids, low boiling point by-products, high boiling point by-products, etc.) by the reaction is obtained in the back end of the reactor.

The mixed gas containing (meth)acrylic acid is generally obtained as (meth)acrylic acid by purification through a process illustrated in FIG. 1.

In detail, the mixed gas containing (meth)acrylic acid contacts an absorption solvent including water in a (meth)acrylic acid absorption tower 100, and is recovered as a (meth)acrylic acid aqueous solution. Further, (meth)acrylic acid-stripped insoluble gas is recycled for a synthesis reaction of (meth)acrylic acid, and a part thereof is incinerated, converted into harmless gas, and discharged. The (meth)acrylic acid aqueous solution is extracted through an extraction tower 200, or is directly to be fed to a water separation tower 300. Water separated from the (meth)acrylic acid aqueous solution is recovered from the upper part of the water separation tower 300, and a (meth)acrylic acid-containing mixture is recovered from the lower portion of the water separation tower 300. The (meth)acrylic acid-containing mixture recovered from the lower portion of the water separation tower 300 is distilled in a high-boiling-point material separation tower 400 to obtain a crude (meth)acrylic acid, which is finally purified in a crystallizer 500 to obtain (meth)acrylic acid.

In this regard, a waste liquid containing Michael adducts such as a dimer to a pentamer of (meth)acrylic acid is obtained from the high-boiling-point material separation tower 400. As a method to increase yield of (meth)acrylic acid, a method of additionally recovering (meth)acrylic acid by feeding the waste liquid to an acrylic acid recovery apparatus 600 and decomposing the Michael adducts in the waste liquid is known.

However, since maleic acid contained in the waste liquid is easily precipitated, it causes the blockage of pipes in the acrylic acid recovery apparatus 600 and raises the viscosity of the waste liquid to reduce the decomposition efficiency of the Michael adducts.

To solve these problems, a method of using a forced circulation type of heat exchanger was suggested. However, this method increases investment costs, because an expensive pump is used in the forced circulation type of heat exchanger. Further, in the method of using the forced circulation type of heat exchanger, high-temperature and high-viscosity waste liquid is used as it is, and therefore, it takes a long time to transfer the waste liquid, which may cause a problem with the pump, and there is also a fatal disadvantage that operation stability of the process is low.

DETAILED DESCRIPTION OF THE INVENTION

Technical Problem

The present disclosure provides a method of preparing (meth)acrylic acid with high process stability, in which Michael adducts included in a waste liquid are decomposed to recover (meth)acrylic acid in an economical and highly efficient manner.

Technical Solution

According to one embodiment of the present disclosure, a method of preparing (meth)acrylic acid by using a reaction distillation apparatus including a reaction distillation tower that has a structure in which a vessel, where decomposition of Michael adducts occurs, is connected to a distillation tower, where distillation of decomposition products occurs, and a natural circulation type of heat exchanger as a heat source of the reaction distillation tower, is provided, the method including the steps of:

feeding a waste liquid, which is discharged in a synthesis process and/or a recovery process of (meth)acrylic acid, to the reaction distillation apparatus; and feeding a gas, separately from the waste liquid, to the lower portion of the heat exchanger.

The waste liquid may be a waste liquid including 5% by weight to 80% by weight of (meth)acrylic acid, 1% by weight to 50% by weight of Michael adducts, 0.1% by weight to 20% by weight of maleic acid, and a remaining amount of other by-products with respect to the total weight of the waste liquid.

The method of preparing (meth)acrylic acid may further include the step of supplying heat to the reaction distillation apparatus. More specifically, in the step of supplying heat, heat may be supplied to the reaction distillation apparatus so that a temperature of the vessel may be adjusted to 130° C. to 170° C.

In the method of preparing (meth)acrylic acid, a reaction residence time may be from 3 hours to 30 hours.

Oxygen, air, an inert gas, or a mixture thereof as the gas may be fed to the heat exchanger. A feeding amount of the gas may be adjusted so that a difference between the highest temperature of the heat exchanger and the temperature of the vessel is 2° C. to 19° C.

The method of preparing (meth)acrylic acid may be performed by using a reaction distillation apparatus, in which a waste oil discharge pump is additionally installed at the lower portion of the vessel, or a reaction distillation apparatus, in which a condenser is additionally installed at the upper portion of the distillation tower.

Meanwhile, according to another embodiment of the present invention, a method of preparing (meth)acrylic acid by using a reaction distillation apparatus including a reaction distillation tower that has a structure in which a vessel, where decomposition of Michael adducts occurs, is connected to a distillation tower, where distillation of decomposition products occurs, and a heat source of the reaction distillation tower, is provided, the method including the steps of:

feeding a waste liquid containing one or more Michael adducts selected from the group consisting of a dimer to a pentamer of (meth)acrylic acid, which is a waste liquid discharged in a synthesis process and/or a recovery process of (meth)acrylic acid, to the reaction distillation apparatus; and producing and recovering (meth)acrylic acid from the Michael adducts by performing decomposition and distillation of the waste liquid, wherein the step of producing and recovering (meth) acrylic acid is performed while the waste liquid is circulated in the reaction distillation apparatus by a gas which is fed separately from the waste liquid.

Advantageous Effects

A method of preparing (meth)acrylic acid according to one embodiment of the present disclosure may decompose Michael adducts contained in a waste liquid in an economical and highly efficient manner, thereby providing (meth) acrylic acid.

BRIEF DESCRIPTION OF THE DRAWINGS

FIG. 1 is a flowchart showing a known purification process of (meth)acrylic acid; and FIG. 2 is a schematic illustration of a reaction distillation apparatus, in which a method of preparing (meth)acrylic acid according to one embodiment of the present invention is performed.

DETAILED DESCRIPTION OF THE EMBODIMENTS

Hereinafter, a method of preparing (meth)acrylic acid according to specific embodiments of the present disclosure will be described in detail.

According to one embodiment of the present disclosure, a method of preparing (meth)acrylic acid by using a reaction distillation apparatus including a reaction distillation tower that has a structure in which a vessel, where decomposition of Michael adducts occurs, is connected to a distillation tower, where distillation of decomposition products occurs, and a natural circulation type of heat exchanger as a heat source of the reaction distillation tower, is provided, the method including the steps of: feeding a waste liquid, which is discharged in a synthesis process and/or a recovery process of (meth)acrylic acid, to the reaction distillation apparatus; and feeding a gas, separately from the waste liquid, to the lower portion of the heat exchanger.

The waste liquid, which is discharged in the synthesis process and the recovery process of (meth)acrylic acid, has high viscosity, and therefore, when this waste liquid is used as a raw material in the reaction distillation method, it tales a long time to transfer the high-viscosity waste liquid, which causes a problem of reduced operation stability.

Accordingly, the present inventors found that circulation of high-viscosity waste liquid may be facilitated by manipulation of supplying a gas to the lower portion of the heat exchanger not only to solve the problem of reduced operation stability due to long-term transfer of the waste liquid, but also to greatly improve thermal efficiency of the heat exchanger, thereby completing the present invention.

Meanwhile, the heat exchanger used in the reaction distillation may include a natural circulation type (thermosyphon) of heat exchanger, a forced circulation type of heat exchanger, etc. Of them, with the natural circulation type of heat exchanger, it is difficult to circulate a high-viscosity solution, but the forced circulation type of heat exchanger is suitable for circulating a high-viscosity solution. However, the forced circulation type of heat exchanger utilizes an expensive pump to increase investment costs.

The waste liquid discharged in the preparation and recovery process of (meth)acrylic acid has high viscosity, and therefore, when this waste liquid is used as a raw material in the reaction distillation method, it is difficult to use the natural circulation type of heat exchanger, and the forced circulation type of heat exchanger including the expensive circulation pump should be employed.

However, according to the method of preparing (meth) acrylic acid, circulation of high-viscosity waste liquid may be facilitated by manipulation of feeding gas to the lower portion of the heat exchanger, and thus it is possible to use the natural circulation type of heat exchanger, leading to reduction of investment costs.

Hereinafter, the method of producing (meth)acrylic acid from a waste liquid including Michael adducts by using the reaction distillation apparatus will be described in detail.

The method of preparing (meth)acrylic acid according to one embodiment may be performed in a reaction distillation apparatus including a reaction distillation tower that has a structure in which a vessel, where decomposition of Michael adducts occurs, is connected to a distillation tower, where distillation of decomposition products occurs, and a heat exchanger as a heat source of the reaction distillation tower.

The reaction distillation tower and the heat exchanger may be connected to each other as in FIG. 2, but the structure of the reaction distillation apparatus where the method of preparing (meth)acrylic acid according to one embodiment is performed is not limited to the structure illustrated in FIG. 2, and omissions, additions, and/or modifications may be made according to the general knowledge of the art to which the present disclosure pertains.

The method of preparing (meth)acrylic acid according to one embodiment includes the step of feeding the waste liquid to the reaction distillation apparatus.

In this regard, the waste liquid to be fed is a waste liquid which is discharged during synthesis of (meth)acrylic acid and recovery of (meth)acrylic acid from a mixed gas containing (meth)acrylic acid, and the waste liquid may be a waste liquid discharged from any one process or a waste liquid obtained by collecting waste liquids discharged from two or more processes.

That is, the waste liquid discharged from the synthesis process of (meth)acrylic acid, the waste liquid discharged from the recovery process of (meth)acrylic acid, or a mixture of the waste liquid discharged from the synthesis process of (meth)acrylic acid and the waste liquid discharged from the recovery process of (meth)acrylic acid may be used.

A composition of the components included in the waste liquid is not particularly limited. However, the waste liquid is allowed to include, for example, 5% by weight to 80% by weight of (meth)acrylic acid, 1% by weight to 50% by weight of Michael adducts, 0.1% by weight to 20% by weight of maleic acid, and a remaining amount of other by-products with respect to the total weight, thereby improving production efficiency of (meth)acrylic acid. The Michael adducts collectively refer to adducts obtained through Michael addition of (meth)acrylic acid, and may include one or more selected from the group consisting of a dimer to a pentamer of (meth)acrylic acid.

The method of preparing (meth)acrylic acid according to one embodiment includes may further include the step of supplying heat to the reaction distillation apparatus for decomposition of Michael adducts and distillation of decomposition products. Specifically, a heating medium heated by an external heat circulator may be fed into the heat exchanger of the reaction distillation apparatus.

The decomposition reaction of the Michael adducts is performed in the vessel, and a temperature of the vessel is preferably maintained constant in order to inhibit side-reactions of the decomposition reaction and to increase decomposition efficiency of the Michael adducts. Therefore, the temperature of the heating medium heated by the external heat circulator may be controlled so as to maintain the vessel at a constant temperature, and then fed into the heat exchanger at a predetermined flow rate.

The waste liquid fed into the reaction distillation apparatus may be circulated between the vessel and the heat exchanger by the circulation type of heat exchanger. In detail, as shown in FIG. 2, the waste liquid contained in the vessel may be transferred to the heat exchanger through the lower portion of the vessel, and the waste liquid heated by the heat exchanger may be fed into the upper portion of the vessel.

In this regard, to achieve a desired yield of (meth)acrylic acid, it is necessary to secure a sufficient residence time for reaction of the waste liquid. First, to secure the sufficient residence time, a vessel having an appropriate size may be employed as the vessel. In order to maintain a predetermined amount of the waste liquid contained in the vessel, a waste oil discharge pump may be additionally installed at the lower portion of the vessel.

The reaction residence time (unit: h) is a value obtained by dividing a reaction operating volume by a discharge flow rate of the waste oil ((reaction operating volume)/(discharge flow rate of waste oil)), and the amount of the liquid waste contained in the vessel and the reaction residence time may be controlled by controlling the discharge amount of the waste oil by using the waste oil discharge pump after employing a vessel having an appropriate size. The reaction residence time may be from about 3 hours to 30 hours, thereby achieving a high yield of (meth)acrylic acid.

The temperature of the vessel may be controlled within an appropriate range for the decomposition reaction of the Michael adducts and the distillation of the decomposition products. For example, heat may be supplied to the reaction distillation apparatus so that the temperature of the vessel may be adjusted to 130° C. to 170° C., and within this range, side-reactions may be inhibited, and decomposition efficiency of the Michael adducts may be increased.

In the known reaction distillation method, the operating temperature or the reaction residence time may be increased in order to increase a conversion rate of Michael adducts. In this case, viscosity of waste oil is increased to decrease the amount of the liquid which is transferred from the heat exchanger to the vessel. As a result, there is a problem that the heat transfer efficiency is significantly lowered and contamination of the pipe is increased.

However, in the method of preparing (meth)acrylic acid according to one embodiment, the conversion rate of Michael adducts may be increased and thermal efficiency of the heat exchanger may be improved by the step of feeding a gas to the lower portion of the natural circulation type of heat exchanger. Specifically, circulation of high-viscosity waste liquid may be facilitated by feeding a gas, separately from the waste liquid, to the heat exchanger. As a result, reduced operation stability due to long-term transfer of the high-viscosity waste liquid may be improved, and it is also possible to use the natural circulation type of heat exchanger in which it is difficult to circulate high-viscosity solutions, thereby saving investment costs.

In particular, thermal efficiency of the heat exchanger may be remarkably improved by the manipulation of feeding a gas to the heat exchanger. In the known reaction distillation method, a heating medium of a very high temperature should be fed in order to maintain the desired temperature of the vessel due to poor circulation of a high-temperature and high-viscosity solution, and for this reason, the internal temperature of the heat exchanger should be maintained at a high temperature.

However, in the method of preparing (meth)acrylic acid according to one embodiment, thermal efficiency is remarkably improved by the manipulation of feeding a gas, and thus the temperature of the vessel may be maintained at the desired temperature even though a heating medium at a lower temperature than that of the known method is fed.

In this regard, the gas and the heating medium may be introduced into different spaces of the heat exchanger. That is, a heat exchanger including a double jacket is used as the heat exchanger, and the heating medium heated in the external heat circulator may be introduced into either the external or internal space, while the gas may be introduced into the other space. The reaction distillation tower may be connected to the heat exchanger such that the waste liquid circulating between the reaction distillation tower and the heat exchanger is introduced into the space to which the gas is introduced.

As the amount (or inflow rate) of the gas introduced into the heat exchanger is increased, thermal efficiency of the heat exchanger is increased, and as a result, a difference between the highest temperature of the heat exchanger and the temperature of the vessel is reduced.

Accordingly, the amount (or inflow rate) of the gas introduced into the heat exchanger may be controlled so that a difference between the highest temperature of the heat exchanger and the temperature of the vessel is 2° C. to 19° C. Specifically, the amount (or inflow rate) of the gas introduced into the heat exchanger may be controlled so that the difference between the highest temperature of the heat exchanger and the temperature of the vessel is 3° C. to 17° C. or 4° C. to 16° C., and therefore, the waste liquid may be efficiently circulated, even though the natural circulation type of heat exchanger is used, and the thermal efficiency of the heat exchanger may be further increased.

However, if the amount of the gas introduced into the heat exchanger is less than as indicated above, the thermal efficiency of the heat exchanger may be decreased, and it is difficult to circulate the waste liquid by the natural circulation type of heat exchanger. In order to introduce an excessively large amount of gas to the heat exchanger, it is required to install a large-scale distillation tower and condenser, and thus it is impossible to operate the existing apparatus and the investment cost may be greatly increased.

The amount or inflow rate of the gas introduced into the heat exchanger may be controlled according to the size of the reaction distillation tower and the amount of the waste liquid contained in the vessel so that the difference between the highest temperature of the heat exchanger and the temperature of the vessel is within the above range.

For example, if the reaction distillation tower is similar in size to a reaction distillation tower used in comparative examples and examples described below, the gas may be introduced at a rate of 10 mL/min to 300 mL/min. Within this range, the above-described effects may be stably secured.

Since the gas introduced into the heat exchanger is introduced for efficient circulation of the waste liquid, a kind of the gas is not particularly limited, as long as it does not react with the waste liquid. For example, in order to further obtain a polymerization-inhibiting effect, the gas may be oxygen, air, an inert gas (e.g., nitrogen, argon, etc.), or a mixture thereof. The air may be atmospheric air or thin air. The thin air refers to air having a lower oxygen content than the atmospheric air and a higher content of other components such as nitrogen, etc. The thin air may be, for example, air that has a reduced concentration of oxygen because the atmospheric air is used in an oxidation reaction and thus oxygen in the atmospheric air is consumed in the oxidation reaction.

As described above, according to the method of preparing (meth)acrylic acid of one embodiment, the waste liquid may be efficiently circulated between the heat exchanger and the vessel by the manipulation of introducing the gas into the heat exchanger. Due to this effect, the waste liquid may remain in the vessel for an appropriate time. As a result, Michael adducts included in the waste liquid may be effectively decomposed. The decomposition products may be distilled through the distillation tower, thereby obtaining (meth)acrylic acid. The distillation tower may include all kinds of distillation towers known in the art to which the present invention pertains.

A condenser for condensation of a distillate which is recovered from the upper portion of the distillation tower may be additionally installed at the upper portion of the distillation tower. Through this condenser, part of the distillate is recovered as a (meth)acrylic acid fraction, and the rest thereof as a reflux liquid may be introduced into the distillation tower.

Further, in order to prevent polymerization of the components (e.g., (meth)acrylic acid, etc.) in the waste liquid in the distillation tower or the vessel, a small amount of a polymerization inhibitor may be added to the upper portion of the distillation tower.

The method of preparing (meth)acrylic acid according to one embodiment may further include steps commonly performed in the art to which the present invention pertains, in addition to the above-described steps. The (meth)acrylic acid recovered from the upper portion of the distillation tower may be introduced into a subsequent treatment process or may be processed into a product, as known in the art to which the present invention pertains.

According to another embodiment of the present invention, a method of preparing (meth)acrylic acid by using a reaction distillation apparatus including a reaction distillation tower that has a structure in which a vessel, where decomposition of Michael adducts occurs, is connected to a distillation tower, where distillation of decomposition products occurs, and a heat source of the reaction distillation tower, is provided, the method including the steps of:

feeding a waste liquid containing one or more Michael adducts selected from the group consisting of a dimer to a pentamer of (meth)acrylic acid, which is a waste liquid discharged in a synthesis process and/or a recovery process of (meth)acrylic acid, to the reaction distillation apparatus; and producing and recovering (meth)acrylic acid from the Michael adducts by performing decomposition and distillation of the waste liquid, wherein the step of producing and recovering (meth)acrylic acid is performed while the waste liquid is circulated in the reaction distillation apparatus by a gas which is fed separately from the waste liquid.

The method of preparing (meth)acrylic acid according to another embodiment may be performed by using the reaction distillation apparatus described in the method of preparing (meth)acrylic acid according to one embodiment, except that a heat source known in the art to which the present invention pertains may be used as the heat source without limitation.

According to the method of preparing (meth)acrylic acid of another embodiment, the waste liquid fed to the reaction distillation apparatus may include Michael adducts, and the Michael adducts may include one or more selected from the group consisting of a dimer to a pentamer of (meth)acrylic acid. The waste liquid may be the waste liquid described as being usable in the above-described method of preparing (meth)acrylic acid according to one embodiment.

In the method of preparing (meth)acrylic acid of another embodiment, decomposition and distillation of the waste liquid may be performed to produce and recover (meth)acrylic acid from the Michael adducts. To this end, heat may be supplied to the reaction distillation apparatus. Operation conditions for the production and recovery of (meth)acrylic acid may be controlled as in the above-described method of preparing (meth)acrylic acid according to one embodiment.

The production and recovery of (meth)acrylic acid may be performed under a gas which is introduced separately from the waste liquid. The gas which is introduced separately from the waste liquid may be the gas as described in the method of preparing (meth)acrylic acid according to one embodiment.

The waste liquid may be efficiently circulated in the reaction distillation apparatus by the gas. In other words, circulation of the high-viscosity waste liquid efficiently occurs by supplying the gas separately from the waste liquid, thereby improving reduced operation stability due to long-term transfer of the high-viscosity waste liquid. It is also possible to use the natural circulation type of heat exchanger in which it is difficult to circulate high-viscosity solutions, thereby saving investment costs.

Additionally, the gas may be introduced into the heat source to increase the conversion rate of the Michael adducts and to improve thermal efficiency of the heat source. The amount of the gas to be introduced may be controlled as in the above-described method of preparing (meth)acrylic acid according to one embodiment.

The method of preparing (meth)acrylic acid according to another embodiment may be performed in the same manner as in the above-described method of preparing (meth)acrylic acid according to one embodiment, unless specifically limited, and may further include steps commonly performed in the art to which the present invention pertains, in addition to the above-described steps.

Hereinafter, the actions and effects of the present invention will be described in more detail with reference to the specific examples. However, these examples are for illustrative purposes only, and the scope of the present invention is not intended to be limited by these examples.

Comparative Example 1: Decomposition of Michael adducts and recovery of acrylic acid Acrylic acid was produced by using a reaction distillation apparatus as shown in FIG. 2 according to the following method. A dual flow type of distillation tower having an ID of 3 cm and consisting of a total of 9 trays was used as a distillation tower, and a top pressure of the distillation tower was adjusted by using a vacuum distillation unit. A natural circulation type of heat exchanger including a double jacket having an inner tube of 1 inch in OD and 1 m in height (reboiler tube length) was used. A heating medium heated in an external heat circulator was passed through the double jacket to supply heat to the heat exchanger. A condenser was installed at the upper portion of the distillation tower such that a distillate extracted from the upper portion of the distillation tower was condensed, part of the distillate as a reflux liquid was introduced into the upper portion of the distillation tower, and the rest thereof was recovered. In order to achieve a desired yield, a vessel having an appropriate size was selected to ensure a proper reaction residence time, and was installed between the distillation tower and the heat exchanger as in FIG. 2.

To recover acrylic acid by decomposing Michael adducts, a waste liquid obtained from the lower portion of a high-boiling-point material separation tower was introduced as a feed into the vessel at a rate of 6.5 g/min. The waste liquid included 44.8% by weight of acrylic acid, 27.8% by weight of acrylic acid dimer, 7.8% by weight of maleic acid, and a remaining amount of other by-products.

To maintain a temperature of the vessel at 142.1° C., a temperature of the heating medium heated in the external heat circulator was controlled and the heating medium was introduced into the double jacket at the same flow rate. In the above process, a reflux ratio was adjusted at 1.0, and a reaction operating pressure of the distillation tower was adjusted at 50 Torr, a height of the liquid contained in the vessel was controlled by using a waste oil discharge pump installed at the lower portion of the vessel so that a reaction residence time was about 15 hours. In this regard, a head height of the liquid was 109 cm.

After operating for about 24 hours by using the apparatus, when the apparatus reached a steady state, the temperature of the heating medium introduced into the heat exchanger and the temperature of the liquid at each point in the heat exchanger were measured, and a mass flow rate of the reaction, such as a flow rate of a distillate, a flow rate of waste oil, etc., compositions of the feed, recovered acrylic acid, and waste oil finally removed by the process were analyzed by GC (gas chromatography) and HPLC (high performance liquid chromatography), and viscosity of the waste oil at 100° C. was measured. A conversion rate of acrylic acid dimer, selectivity of acrylic acid, and yield of acrylic acid were calculated through the compositions of the feed, recovered acrylic acid, and waste oil.

Conversion rate of acrylic acid dimer (%)=(mass of decomposed acrylic acid dimer)/(mass of acrylic acid dimer before decomposition)*100  (1)

Selectivity of acrylic acid (%)=(mass of produced acrylic acid)/(mass of acrylic acid dimer before decomposition)*100  (2)

Yield of acrylic acid (%)=(conversion rate of acrylic acid dimer)*(selectivity of acrylic acid)  (3)

Reaction residence time (hr)=(reaction operating volume)/(waste oil discharge flow rate)  (4)

Example 1: Decomposition of Michael adducts and recovery of acrylic acid

Acrylic acid was obtained from the waste liquid including Michael adducts by operating the reaction distillation apparatus in the same manner as in Comparative Example 1, except that oxygen was introduced into the lower portion of the heat exchanger at a rate of 70 mL/min, and the temperature of the vessel was controlled to 142.5° C. to maintain the conversion rate of the acrylic acid dimer at the same level as in Comparative Example 1.

Example 2: Decomposition of Michael adducts and recovery of acrylic acid

Acrylic acid was obtained from the waste liquid including Michael adducts by operating the reaction distillation apparatus in the same manner as in Comparative Example 1, except that oxygen was introduced into the lower portion of the heat exchanger at a rate of 200 mL/min, and the temperature of the vessel was controlled to 143.0° C. to maintain the conversion rate of the acrylic acid dimer at the same level as in Comparative Example 1.

The main process conditions of Comparative Example 1 and Examples 1 and 2, the temperature at various points in the apparatus at the steady state, the conversion rate of acrylic acid dimer, the selectivity of acrylic acid, and the yield of acrylic acid are shown in Table 1 below.

TABLE 1

| | Comparative Example 1 | Example 1 | Example 2 |
|---|---|---|---|
| O$_2$ feed rate [mL/min] | 0 | 70 | 200 |
| Vessel temperature [° C.] | 142.1 | 142.5 | 143.0 |
| Conversion rate of acrylic acid dimer [%] | 52.8 | 52.8 | 52.6 |
| Selectivity of acrylic acid [%] | 71.2 | 72.8 | 73.9 |
| Yield of acrylic acid [%] | 37.6 | 38.4 | 38.9 |
| Waste oil viscosity [cP at 100° C.] | 51 | 47 | 51 |
| Feed temperature of heating medium [° C.] | 179.8 | 172.6 | 168.8 |
| Internal temperature of heat exchanger [° C.] 102 cm from lower portion | 145.5 | 143.0 | 143.2 |
| 75 cm from lower portion | 152.9 | 146.7 | 146.7 |
| 50 cm from lower portion | 161.4 | 150.4 | 147.6 |
| 25 cm from lower portion | 149.8 | 146.3 | 145.8 |
| ΔT1 [° C.] (highest temperature in heat exchanger - vessel temperature) | 19.3 | 7.9 | 4.6 |
| ΔT2 [° C.] (feed temperature of heating medium - vessel temperature) | 37.7 | 30.1 | 25.8 |

Referring to Table 1, when the gas, for example, oxygen, was introduced, separately from the waste liquid, into the heat exchanger under the process conditions which were controlled to show the conversion rate of the acrylic acid dimer at the same level, the feed temperature of the heating medium was decreased, and a difference (ΔT2) between the feed temperature of the heating medium and the temperature of the vessel, and a difference (ΔT1) between the highest temperature of the heat exchanger and the temperature of the vessel, were decreased, and as a result, thermal efficiency of the heat exchanger was increased.

REFERENCE NUMERALS

100: Absorption tower
150: Acetic acid absorption tower

200: Extraction tower
300: Water separation tower
350: Phase separation tank
400: High-boiling-point material separation tower
500: Crystallizer
600: Acrylic acid recovery apparatus
PW: Process water
CAA: Crude (meth)acrylic acid
HPAA: High-purity (meth)acrylic acid

The invention claimed is:

1. A method of preparing (meth)acrylic acid by using a reaction distillation apparatus comprising a reaction distillation tower, and a natural circulation type of heat exchanger as a heat source for the reaction distillation tower, wherein the reaction distillation tower has a structure in which a vessel, where decomposition of Michael adducts occurs, is connected to a distillation tower, where distillation of decomposition products occurs, the method comprising the steps of:

feeding a waste liquid, which is discharged in a synthesis process and/or a recovery process of (meth)acrylic acid, to the reaction distillation apparatus after passing through the heat exchanger, wherein the waste liquid is fed to a lower portion of the heat exchanger via a first input port;

feeding a gas, separately from the waste liquid via a second input port, to the lower portion of the heat exchanger, and producing and recovering (meth)acrylic acid while the waste liquid is circulated in the reaction distillation apparatus by the gas which is fed separately from the waste liquid.

2. The method of preparing (meth)acrylic acid of claim 1, wherein the waste liquid comprises 5% by weight to 80% by weight of (meth)acrylic acid, 1% by weight to 50% by weight of Michael adducts, 0.1% by weight to 20% by weight of maleic acid, and a remaining amount of other by-products with respect to the total weight of the waste liquid.

3. The method of preparing (meth)acrylic acid of claim 1, further comprising the step of supplying heat to the reaction distillation apparatus.

4. The method of preparing (meth)acrylic acid of claim 1, wherein the method is performed by using a reaction distillation apparatus further comprising a waste oil discharge pump installed at a lower portion of the vessel.

5. The method of preparing (meth)acrylic acid of claim 1, wherein the reaction residence time is from 3 hours to 30 hours.

6. The method of preparing (meth)acrylic acid of claim 3, wherein heat is supplied to the reaction distillation apparatus so that the temperature of the vessel is adjusted to 130° C. to 170° C.

7. The method of preparing (meth)acrylic acid of claim 1, wherein the amount of the gas introduced into the lower portion of the heat exchanger is adjusted so that the difference between the highest temperature of the heat exchanger and the temperature of the vessel is 2° C. to 19° C.

8. The method of preparing (meth)acrylic acid of claim 1, wherein the gas introduced into the heat exchanger is selected from oxygen, air, an inert gas, or a mixture thereof.

9. The method of preparing (meth)acrylic acid of claim 1, wherein the method is performed by using a reaction distillation apparatus further comprising a condenser installed at the upper portion of the distillation tower.

10. A method of preparing (meth)acrylic acid by using a reaction distillation apparatus including a reaction distillation tower and a heat source for the reaction distillation tower, wherein the reaction distillation tower has a structure in which a vessel, where decomposition of Michael adducts occurs, is connected to a distillation tower, where distillation of decomposition products occurs, the method comprising the steps of:

feeding a waste liquid containing one or more Michael adducts selected from the group consisting of a dimer, a trimer, a tetramer and a pentamer of (meth)acrylic acid, which is a waste liquid discharged in a synthesis process and/or a recovery process of (meth)acrylic acid, to the reaction distillation apparatus; and producing and recovering (meth)acrylic acid from the Michael adducts by performing decomposition and distillation of the waste liquid, wherein the step of producing and recovering (meth)acrylic acid is performed while the waste liquid is circulated in the reaction distillation apparatus by a gas which is fed separately from the waste liquid.

* * * * *